United States Patent [19]
Santos

[11] 3,959,960
[45] June 1, 1976

[54] TENSIONING, TWISTING AND CUTTING DEVICE FOR SUTURES

[76] Inventor: Manuel V. Santos, 126 Pulaski St., Newark, N.J. 07105

[22] Filed: Mar. 12, 1975

[21] Appl. No.: 557,461

[52] U.S. Cl. .............................. 57/22; 128/334 R
[51] Int. Cl.² ................ B65H 69/06; A61B 17/04
[58] Field of Search ................... 57/22, 23, 159; 128/334 R, 334 C

[56] References Cited
UNITED STATES PATENTS
| | | | |
|---|---|---|---|
| 1,675,400 | 7/1928 | Young | 57/22 |
| 3,729,913 | 5/1973 | Wray | 57/22 |

*Primary Examiner*—John Petrakes
*Attorney, Agent, or Firm*—Carella, Bain, Gilfillan & Rhodes

[57] ABSTRACT

This invention relates to surgical instruments used, for example, in approximation of the sternum after median sternotomy. The device according to this invention is utilized to tighten applied sternal sutures, such as wires, by first winding up the sutures on a spool, then twisting the sutures for fixation and to provide an appropriate final tension. A cutting mechanism is included for severing the sutures so as to leave a short twisted segment, resulting in a joint secure against slippage. Waste sutures are stripped from the spool against a stripping plate by axial translation of the spool. A crank and sleeve may be included to facilitate twisting the sutures for fixation and final tensioning. An optional ratchet or similar mechanism may be used to prevent unwinding of the sutures from the spool during operation.

19 Claims, 16 Drawing Figures

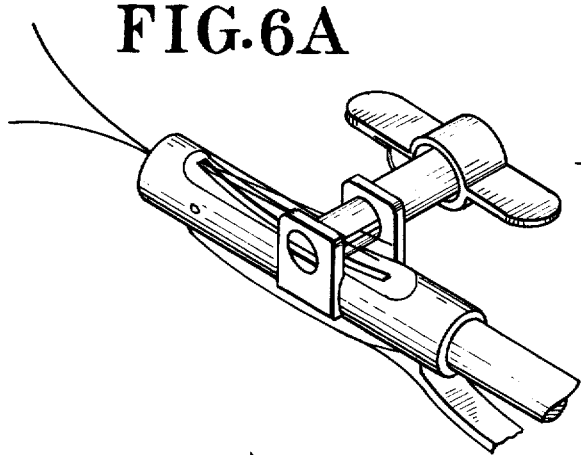
FIG. 6A
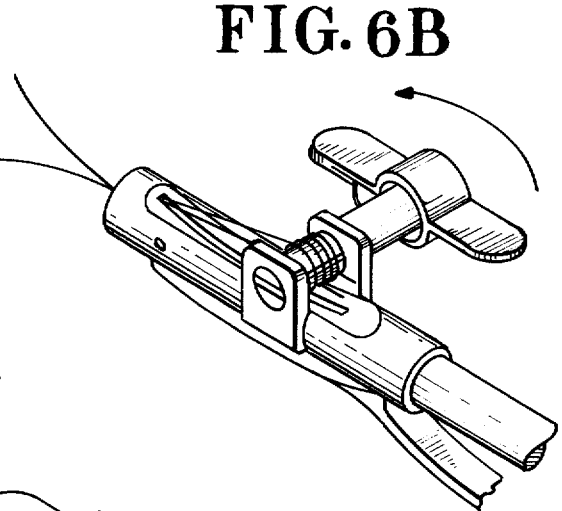
FIG. 6B
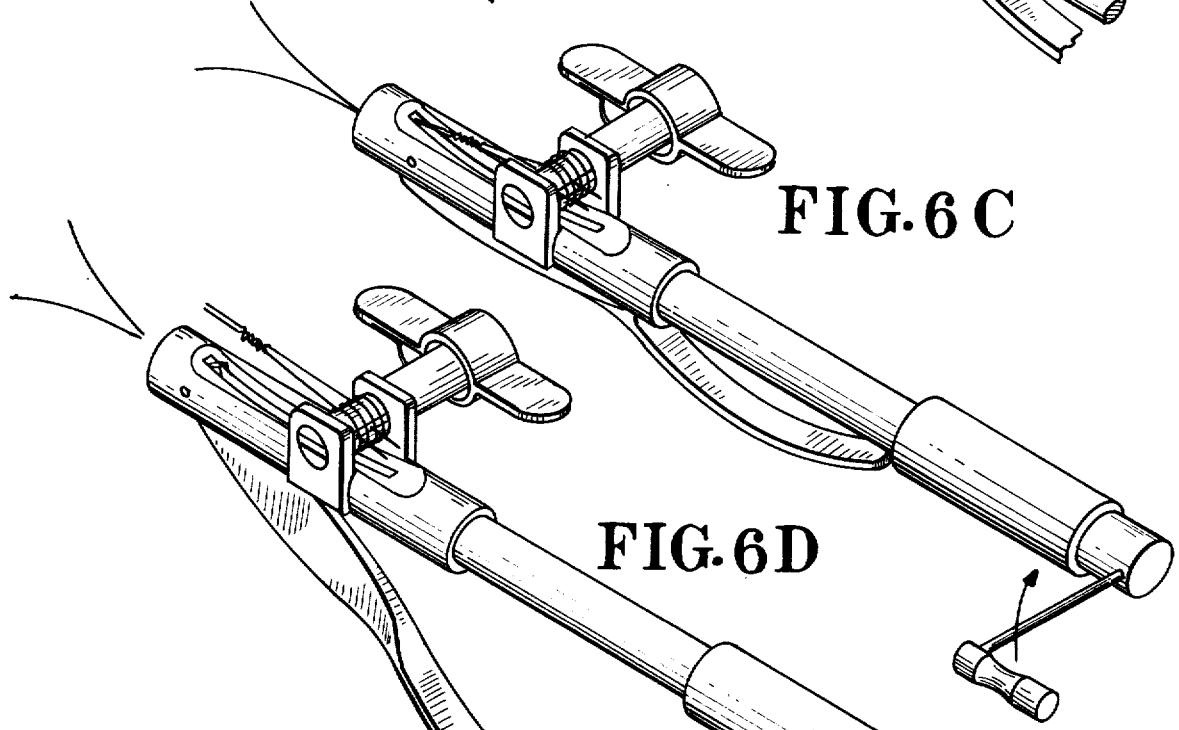
FIG. 6C
FIG. 6D
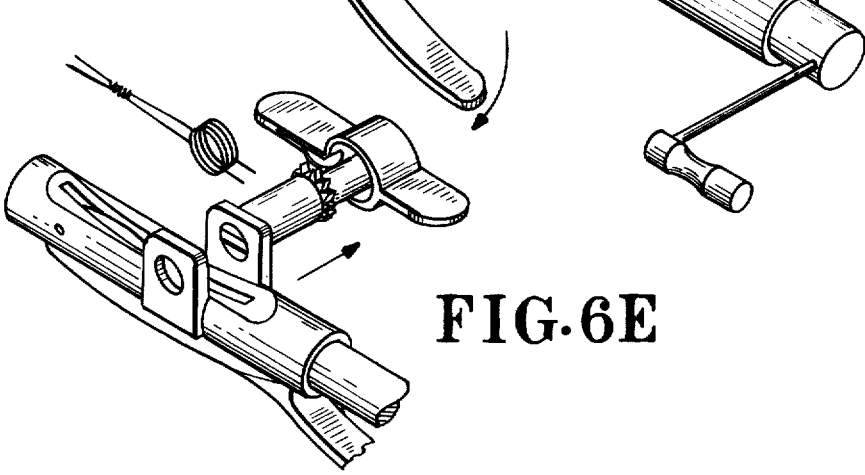
FIG. 6E

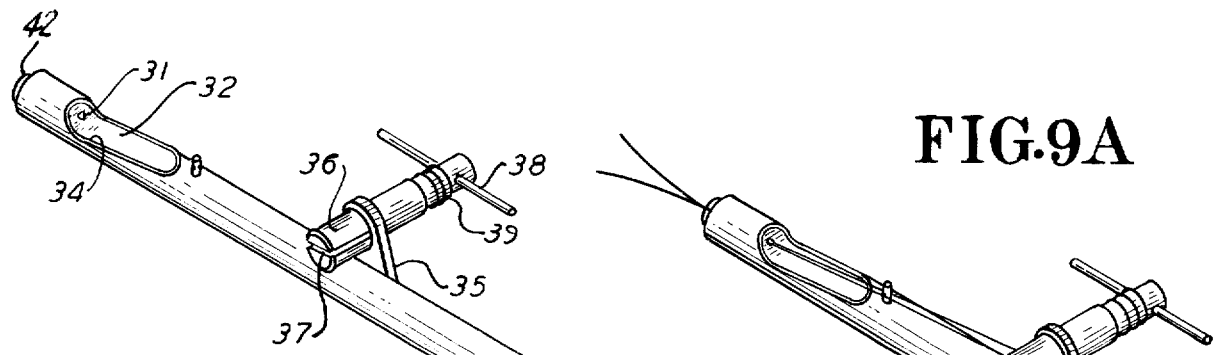
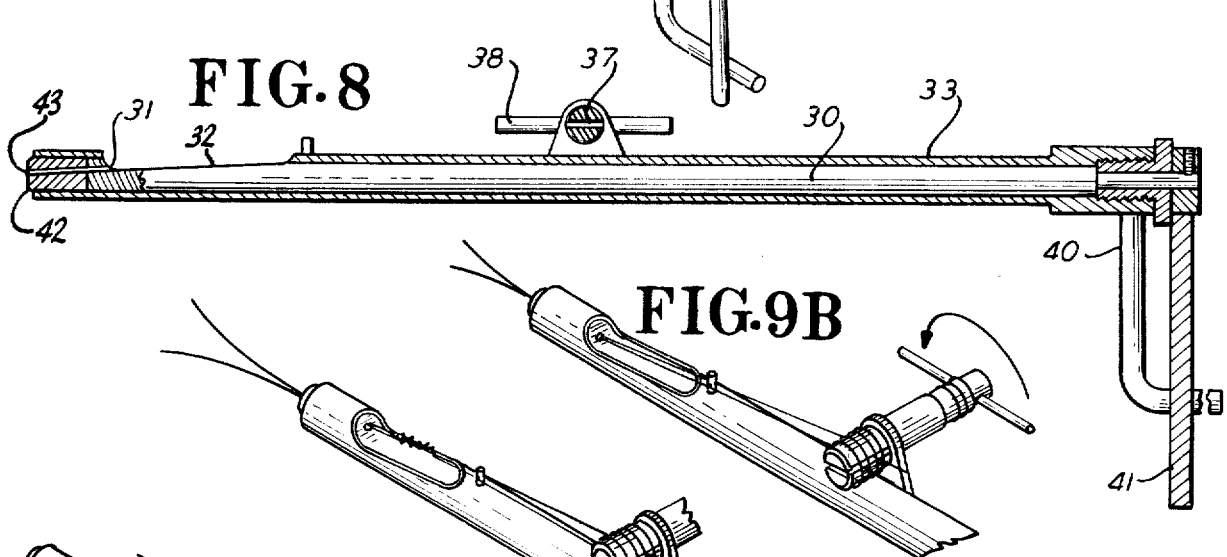
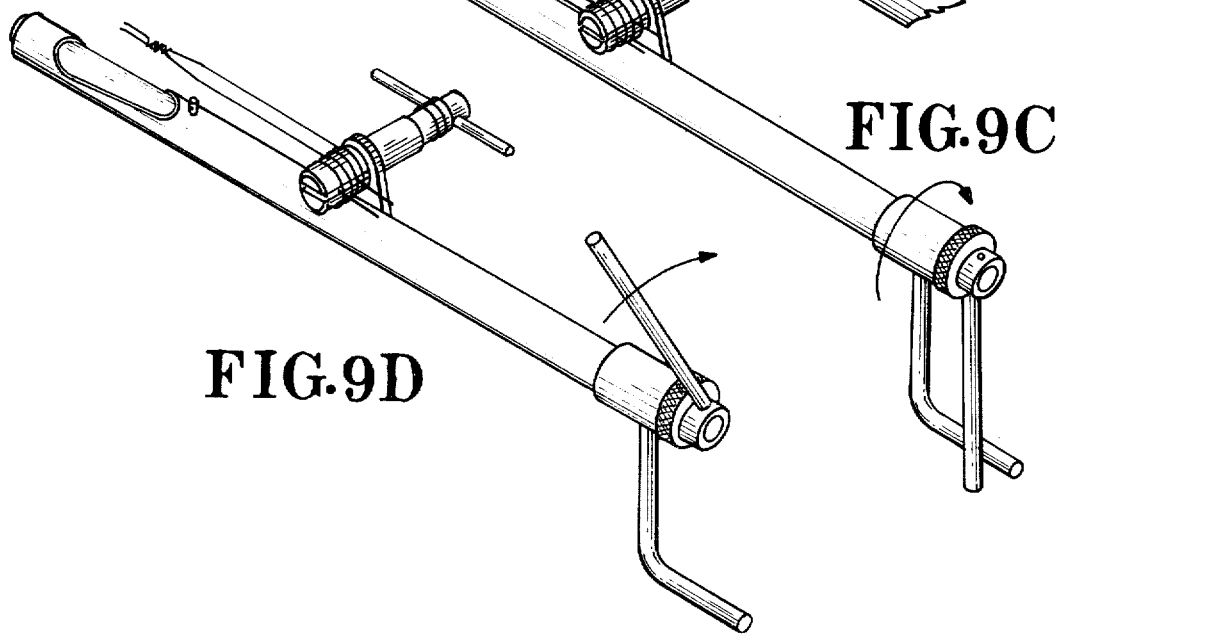

TENSIONING, TWISTING AND CUTTING DEVICE FOR SUTURES

BACKGROUND OF THE INVENTION

1. Field of the Invention

The present invention relates to surgical instruments generally, and in particular to devices used for joining, tensioning, fixing and severing sutures. This invention finds application, for example, with stainless steel sutures in sternotomy closure.

2. Description of the Prior Art

The prior art includes manual techniques in which suture wires are crossed, twisted, tightened and cut. The twisted segment, measuring approximately 1 cm. in length, is then further tightened, trimmed and bent into adjacent tissue. Although this method is widely employed, occasional difficulties are encountered relating to the manual technique for suture wire application and approximation. Asymmetric twisting of the wire may cause wire buckling, metal fatigue and possible wire fracture. Incomplete wire fixation can result in motion between the approximated sides of the sternum with resultant post-operative pain and possible dehiscence.

Nylon bands have been used for closure, but these were found unacceptable by some workers because of an increased incidence of complications and sternal infection.

Small stainless steel plates have also been utilized for fixation of wire sutures, but this technique requires three additional instruments and components in addition to the wire sutures, and cutting and trimming of the wire sutures is still necessary. The principle of applying controlled tension to close the sternum has led to satisfactory sternal approximation in a small series of patients, however.

SUMMARY OF THE INVENTION

The primary object of the present invention is to provide a new device for joining, tensioning, fixing and severing sutures in, for example, approximation of the sternum after median sternotomy, using stainless steel sutures.

The device according to this invention includes a shaft having stripping and retaining plates, a channel and a lumen. The sutures are fed through the lumen to a slotted spool which extends through holes in the stripping and retaining plates and which serves to wind up the sutures so as to provide an initial degree of tension. Means are provided for rotating the spool to wind up the sutures, and an optional ratchet or similar mechanism may be utilized to prevent unwinding of the sutures from the spool during use. The device itself is rotated to twist the sutures together, thereby fixing the sutures and imparting an appropriate final degree of tension; this operation is facilitated by provision of a crank, for rotating the device, and a sleeve, for holding the device during rotation. A cutting mechanism is included to sever the twisted ends of the sutures, thereby leaving a short twisted segment for fixation. The spool is mounted in such a way that the stripping and retaining plates serve to retain the sutures laterally on the spool during operation. The spool can be axially translated so that the stripping plate strips waste sutures from the spool.

BRIEF DESCRIPTION OF THE DRAWINGS

FIG. 2 also shows the orientation of the sections presented in FIGS. 3 and 4.

FIG. 4 shows the orientation of the section of FIG. 5.

FIGS. 6A through 6E depict operation of the device for tensioning and cutting sutures according to the present invention.

FIG. 7 is an isometric view of a alternative embodiment of the invention.

FIG. 8 is a sectional view of the alternative embodiment. FIGS. 9A through 9D depict the operation of the alternative embodiment of the invention.

DESCRIPTION OF THE INVENTION

Figure 1:
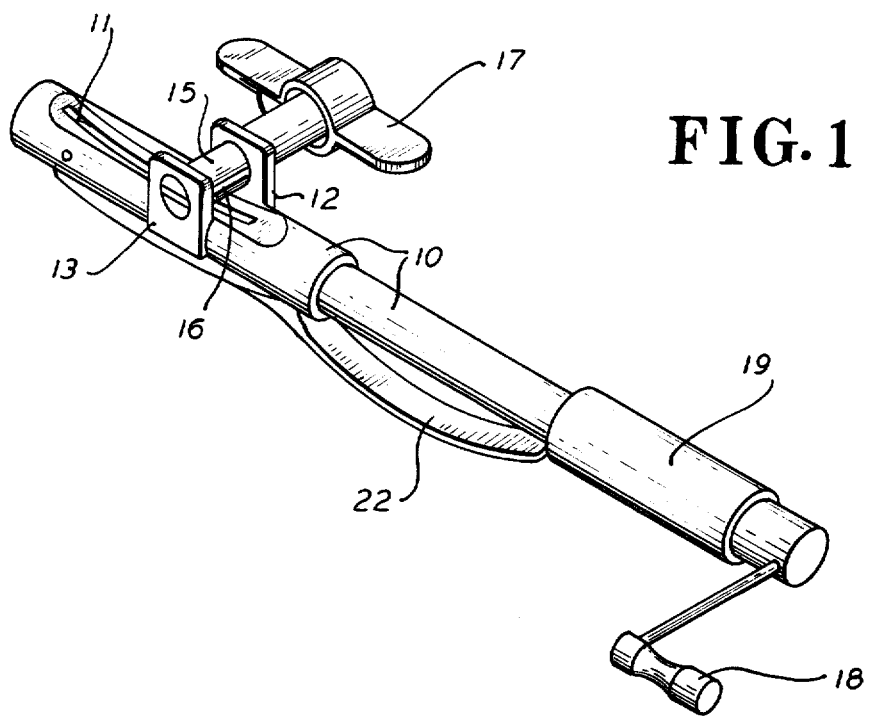
FIG. 1 is an isometric view of a complete device for tensioning and cutting sutures according to the present invention.
Figure 2:
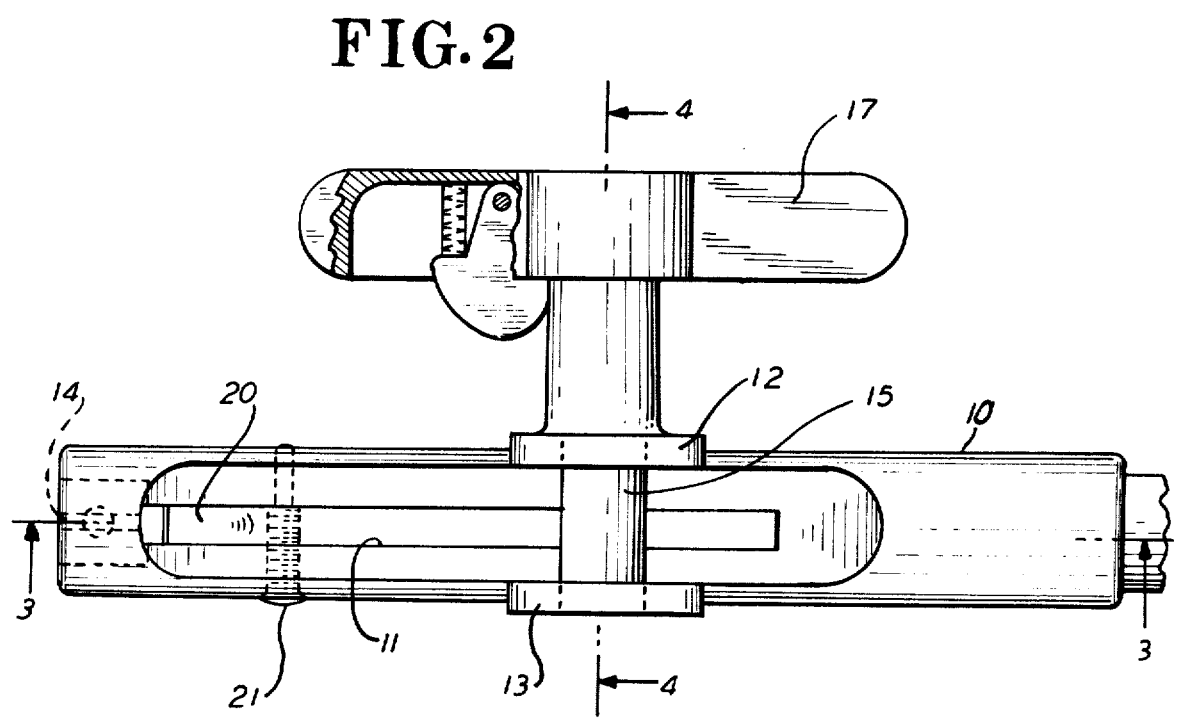
FIG. 2 shows the arrangement of the channel, stripping and retaining plates, key and pawl.

The device according to the present invention can be understood by referring to the embodiment depicted in FIG. 1. It consists of a shaft 10 having a channel 11 together with integral stripping plate 12 and integral retaining plate 13. Not visible in FIG. 1, but shown by the dashed lines in FIG. 2, is the lumen 14 which extends from the front of the shaft 10 into the channel 11.

A spool 15 extends through holes in the stripping and retaining plates 12 and 13. The spool 15 contains a slot 16, visible in FIG. 1, which serves to receive and retain the sutures. Attached to the spool 15 is a key 17, by which the operator of the device rotates the spool 15 to wind up the sutures and thereby to provide an initial degree of tension. Key 17 is representative of one possible means of rotating the spool to wind up the sutures.

The process of rotating the shaft to twist the sutures together to provide fixation and a final degree of tension is facilitated by crank 18, visible in FIG. 1. Sleeve 19, which is rotatably secured to the shaft, provides a convenient surface for grasping the instrument during operation of the crank 18.

Figure 3:
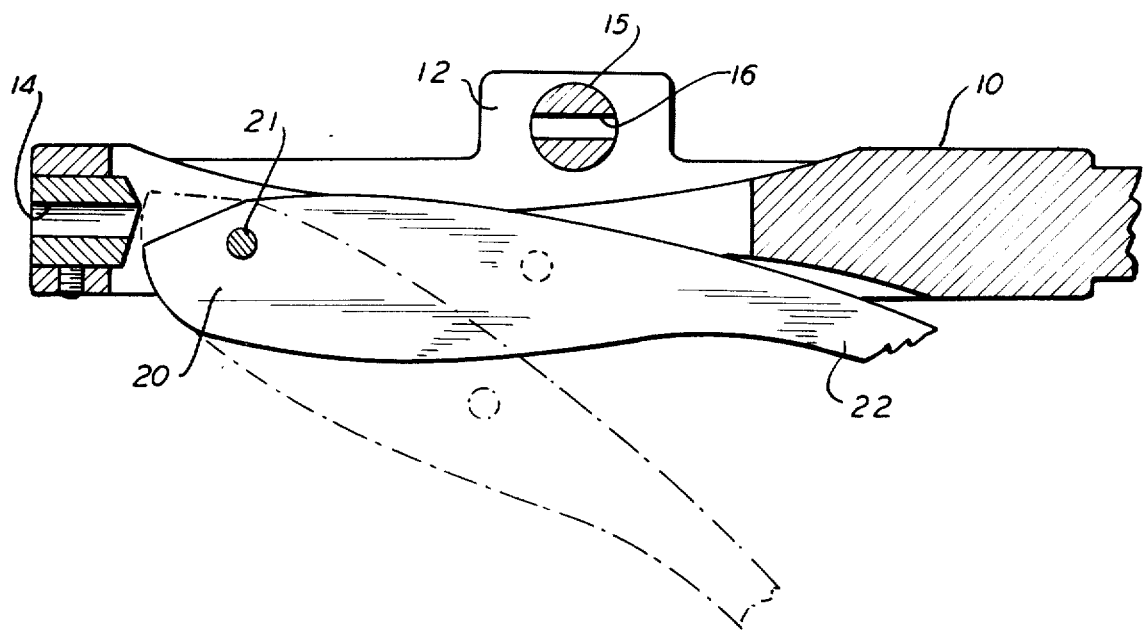
FIG. 3 is a sectional view depicting the cutting mechanism.

FIG. 3 is a cross-sectional view of the shaft 10 showing details of the cutter 20. It will be noted that the cutter 20 is pivotally secured to the shaft by a pin 21, and it includes portions defining an arm 22. In operation, arm 22 is moved away from shaft 10 to cut the sutures where they exit the lumen 14.

Figure 4:
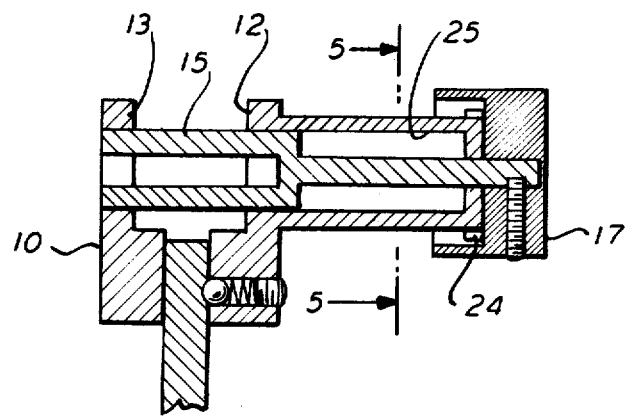
FIG. 4 is a sectional view showing the spool and its associated ratchet wheel and pawl mechanism. The operation of the stripping mechanism, involving retraction of the spool, is also apparent from FIG. 4. In addition.

FIG. 4 is a cross-sectional view showing details of the spool 15 and its associated components. Stripping plate 12 and retaining plate 13 are visible in FIG. 4 as is ratchet wheel 24 which, in cooperation with pawl 23 (visible in FIG. 5), serves to restrict the rotation of spool 15 to substantially unidirectional rotation. It will be apparent to those skilled in the art that other mechanisms than the pawl and ratchet wheel can be utilized to limit rotation of the spool to substantially unidirectional rotation.

In FIG. 4, it can be seen that spool 15 extends through holes in stripping plate 12 and retaining plate 13. During the process of winding sutures up on the spool, stripping plate 12 and retaining plate 13 serve to retain the sutures laterally on the spool 15. However, after the sutures have been severed by operation of the cutter 20, waste sutures can readily by stripped from the spool 15 by pulling key 17 away from the shaft 10, causing spool 15 to retract into cylinder 25. Waste sutures are thereby stripped from spool 15 by the action of stripping plate 12.

Figure 5:
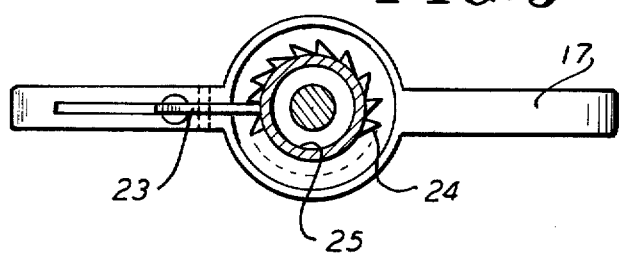
FIG. 5 is a sectional view showing details of the ratchet wheel and pawl mechanism.

FIG. 5 is a cross-section showing details of the pawl 23 and ratchet wheel 24, which cooperate to limit rotation of spool 15 to substantially undirectional rotation.

FIGS. 6A through 6E show, in sequence, the operation of the completed instrument for tensioning and cutting sutures.

In FIG. 6A, the two ends of the suture are shown having been fed through the lumen into the channel and through the slot of the spool.

The next operation, as shown in FIG. 6B, is rotation of the key to cause the spool to rotate, and thereby to wind up the ends of the suture on the spool to provide an initial degree of tension.

FIG. 6C shows how the device is rotated about a longitudinal axis to twist together the ends of the suture for fixation and to impart an appropriate final degree of tension.

In FIG. 6D, the arm of the cutter has been moved away from the shaft so as to sever the sutures where they exit the lumen into the channel, thereby leaving a short segment, typically 9 m.m. with approximately five twists of the wire within this length.

Finally, FIG. 6E shows the process of stripping the waste sutures from the spool by pulling the key outward. The spool is thereby retracted into the cylinder, causing waste sutures to be stripped off against the stripping plate.

FIG. 7 shows, in isometric view, an embodiment of the present invention adapted for use in dental surgery. In FIG. 8, this same embodiment is shown in cross-section. Referring to FIGS. 7 and 8, it can be seen that shaft 30 containing lumen 31 and channel 32, is surrounded by a tube 33, which is secured to the shaft 30 in such a way that shaft 30 can be rotated relative to tube 33. Tube 33 has an opening 34 which exposes channel 32 when shaft 30 is in a first rotational position relative to tube 33. A plug 42 is affixed within tube 33 so as to abut the end of shaft 30 containing the lumen 31. Plug 42 contains a second lumen 43. Both lumen 31 and second lumen 43 are located and oriented so that their intersection, where plug 42 abuts the end of shaft 30, is displaced from the axis of shaft 30, so that when shaft 30 is in the first rotational position relative to tube 33, lumen 31 communicates with second lumen 42 so as to provide a passage for sutures through plug 43 and into and through opening 34. By rotating the shaft 30 to a second rotational position relative to tube 33, lumen 31 no longer communicates with second lumen 43, and the sutures may thereby be cut by the shearing action resulting from such rotation.

Handle 40, affixed to the end of tube 33 opposite from the plug 42, and rod 41, affixed to the end of shaft 30 opposite from the lumen 31, cooperatively serve as means for twisting the sutures and also as means for rotating the shaft, relative to the tube, to cut the sutures. By turning handle 40, rod 41 is engaged and the entire instrument, including both shaft 30 and tube 33, is caused to rotate about a longitudinal axis, thereby twisting the sutures together to provide fixation and a final degree of tension. By holding handle 40 while rotating rod 41, the shaft 30 is caused to rotate relative to tube 33, thereby cutting the sutures.

Bracket 35, affixed to tube 33 immediately to the rear of opening 34, serves to rotatably secure spool 36. Spool 36 incorporates a slot 37 for receiving and retaining the sutures. Key 38 is provided to facilitate rotation of spool 36 by an operator.

Clamping spring 39 is provided to limit the rotational motion of spool 36 to substantially uni-directional rotation. One end of clamping spring 39 is affixed to bracket 35, and the other end is free. Clamping spring 39 surrounds, in close proximity, a portion of spool 36 that extends through bracket 35. When spool 36 is turned in such a direction as to tighten clamping spring 39, rotation is prevented. Rotation of spool 36 in a direction opposite to that corresponding to tightening of clamping spring 39 is not impeded.

FIGS. 9A through 9D show, in sequence, the operation of the alternative embodiment for tensioning, twisting and cutting sutures.

In FIG. 9A, the two ends of the suture are shown having been fed through the second lumen in the plug, through the lumen into the channel, through the opening of the tube, and through the slot of the spool.

The next operation, as shown in FIG. 9B, is rotation of the key to cause the spool to rotate, and thereby to wind up the ends of the suture on the spool to provide an initial degree of tension.

FIG. 9C shows how the instrument is rotated about a longitudinal axis, by operation of the handle and engagement of the rod by the handle, to twist together the ends of the suture for fixation and to impart an appropriate final degree of tension.

In FIG. 9D, the rod has been rotated relative to the handle, thereby cutting the twisted sutures.

The alternative embodiment shown in FIGS. 7, 8, and 9A–9D incorporates no means for stripping waste sutures from the spool, but it is apparent that the translatable spool arrangement of FIG. 4 could be used. In such a case, the stripping and retaining plates could be mounted to the tube 33, replacing bracket 35.

It will be understood by those skilled in the art that many modifications and variations of the present invention may be made without departing from the spirit and the scope thereof.

What is claimed is:

1. A tensioning, twisting and cutting device for sutures, comprising:
    a. an elongate shaft having lumen means, at an end thereof, for passing the sutures through;
    b. the shaft having a channel communicating with the lumen means;
    c. rotatable spool means, proximate the channel, for winding up the sutures to provide an initial degree of tension;
    d. the spool means having a slot to receive the sutures;
    e. means for rotating the spool means to wind up the sutures on the spool means;
    f. means for twisting the sutures together to provide fixation and a final degree of tension; and
    g. cutting means, for cutting the sutures.

2. A tensioning, twisting and cutting device for sutures, as recited in claim 1, further comprising:
    a. means for limiting rotation of the spool means to substantially unidirectional rotation.

3. A tensioning, twisting and cutting device for sutures, as recited in claim 1, wherein the means for rotating the spool means comprises:
   a. a key.

4. A tensioning, twisting and cutting device for sutures, as recited in claim 1, wherein the cutting means are pivotally secured to the shaft within the channel intermediate the lumen means and the spool means.

5. A tensioning, twisting and cutting device for sutures, as recited in claim 4, wherein the rotatable spool means are rotatably secured to the shaft proximate the channel.

6. A tensioning, twisting and cutting device for sutures, as recited in claim 5, further comprising:
   a. means for stripping waste sutures from the spool means.

7. A tensioning, twisting and cutting device for sutures, as recited in claim 6, wherein the means for stripping waste sutures from the spool means comprises:
   a. stripping plate means for stripping waste sutures from the spool means;
   b. the stripping plate means integral to the shaft adjacent the channel; and
   c. the stripping plate means having a hole through which the spool means may be drawn by axial translation thereof, whereby waste sutures may be stripped from the spool means by the stripping plate means.

8. A tensioning, twisting and cutting device for sutures, as recited in claim 7, further comprising:
   a. retaining plate means for retaining sutures on the spool during operation prior to stripping;
   b. the retaining plate means integral to the shaft adjacent the channel, and opposite the channel from the stripping plate means;
   c. the retaining plate means having a hole through which the spool means may be drawn by axial translation thereof, whereby waste sutures may be stripped from the spool means by the stripping plate means.

9. A tensioning, twisting and cutting device for sutures, as recited in claim 8, further comprising:
   a. means for limiting rotation of the spool means to substantially unidirectional rotation;
   b. the means for limiting rotation of the spool means to substantially unidirectional rotation including a ratchet wheel and pawl.

10. A tensioning, twisting and cutting device for sutures, as recited in claim 9, wherein the means for twisting the sutures together comprises:
    a. a crank secured to the shaft at the end opposite the lumen means, whereby the shaft may be caused to rotate about a longitudinal axis.

11. A tensioning, twisting and cutting device for sutures, as recited in claim 10, further comprising:
    a. A sleeve means, rotatably secured to the shaft intermediate the crank and the channel, for being held by an operator while operating the crank to rotate the shaft.

12. A tensioning, twisting and cutting device for sutures, as recited in claim 1, further comprising:
    a. an elongate tube surrounding the shaft and having an internal surface substantially complementary to the external surface of the shaft;
    b. the tube rotatably secured to the shaft and having an opening located so as to expose the channel when the tube is in a first rotational position relative to the shaft;
    c. a plug fixedly secured within the tube and abutting the shaft at the lumen means;
    d. the plug having second lumen means communicating with the lumen means when the shaft is in the first rotational position, and occluded by the shaft when the shaft is in a second rotational position; and
    e. means for rotating the shaft, relative to the tube, from the first rotational position to the second rotational position, whereby the sutures may be cut by the shearing action of the first lumen means against the second lumen means.

13. A tensioning, twisting and cutting device for sutures, as recited in claim 12, wherein the rotatable spool means are rotatably secured to the tube adjacent an end of the open distal the lumen means.

14. A tensioning, twisting and cutting device for sutures, as recited in claim 13, further comprising:
    a. means for stripping waste sutures from the spool means.

15. A tensioning, twisting and cutting device for sutures, as recited in claim 14, wherein the means for stripping waste sutures from the spool means comprises:
    a. stripping plate means for stripping waste sutures from the spool means;
    b. the stripping plate means secured to the tube adjacent an end of the opening distal the lumen means;
    c. the stripping plate means having a hole through which the spool means may be drawn by axial translation thereof, whereby waste sutures may be stripped from the spool means by the stripping plate means.

16. A tensioning, twisting and cutting device for sutures, as recited in claim 15, further comprising:
    a. retaining plate means for retaining sutures on the spool during operation prior to stripping;
    b. the retaining plate means secured to the tube in juxtaposition to the stripping plate means;
    c. the retaining plate means having a hole through which the spool means may be drawn by axial translation thereof, whereby waste sutures may be stripped from the spool means by the stripping plate means.

17. A tensioning, twisting and cutting device for sutures, as recited in claim 16, further comprising:
    a. means for limiting rotation of the spool means to substantially unidirectional rotation;
    b. the means for limiting rotation of the spool means to substantially unidirectional rotation including a clamping spring having one end fixedly secured to a predetermined member.

18. A tensioning, twisting and cutting device for sutures, as recited in claim 17, wherein the means for rotating the shaft, relative to the tube, comprises:
    a. a rod secured to the shaft at the end opposite the lumen means.

19. A tensioning, twisting and cutting device for sutures, as recited in claim 18, wherein the means for twisting the sutures together comprises:
    a. a handle secured to the tube at the end opposite the plug;
    b. the handle engaging the rod to limit rotation of the tube relative to the shaft, whereby operation of the handle causes the shaft and the tube to rotate together.

* * * * *